(12) United States Patent
Tanga

(10) Patent No.: US 6,525,343 B1
(45) Date of Patent: Feb. 25, 2003

(54) MICRO-CHIP FOR CHEMICAL REACTION

(75) Inventor: Michifumi Tanga, Kudamatsu (JP)

(73) Assignee: Toyo Kohan Co., Ltd., Tokyo (JP)

( * ) Notice: Subject to any disclaimer, the term of this patent is extended or adjusted under 35 U.S.C. 154(b) by 0 days.

(21) Appl. No.: 09/890,877

(22) PCT Filed: Feb. 16, 2000

(86) PCT No.: PCT/JP00/00867

§ 371 (c)(1),
(2), (4) Date: Dec. 4, 2001

(87) PCT Pub. No.: WO00/48724

PCT Pub. Date: Aug. 24, 2000

(30) Foreign Application Priority Data

Feb. 18, 1999 (JP) .............................. 11-040689

(51) Int. Cl.[7] ....................... H01L 23/58; H01L 31/312; H01L 29/82; H01L 29/84
(52) U.S. Cl. .............................. 257/77; 257/48; 257/77; 257/252; 257/253; 257/414; 257/798; 257/930
(58) Field of Search ........................... 257/48, 77, 930, 257/798, 414, 252, 253

(56) References Cited

U.S. PATENT DOCUMENTS

| 5,580,523 | A | | 12/1996 | Bard | |
|---|---|---|---|---|---|
| 5,639,423 | A | | 6/1997 | Northrup et al. | |
| 5,663,595 | A | * | 9/1997 | Shiomi et al. | 257/712 |
| 5,821,399 | A | * | 10/1998 | Zelin | 73/1.02 |
| 5,849,208 | A | * | 12/1998 | Hayes et al. | 216/94 |
| 5,858,195 | A | | 1/1999 | Ramsey | |
| 2001/0008613 | A1 | * | 7/2001 | Kaltenbach et al. | 422/101 |
| 2001/0023824 | A1 | * | 9/2001 | Manz et al. | 204/453 |
| 2001/0055812 | A1 | * | 12/2001 | Mian et al. | 436/45 |
| 2002/0008030 | A1 | * | 1/2002 | Ramsey | 204/453 |

FOREIGN PATENT DOCUMENTS

JP         7232056 A          9/1995

* cited by examiner

*Primary Examiner*—Amir Zarabian
*Assistant Examiner*—Ida M. Soward
(74) *Attorney, Agent, or Firm*—Browdy and Neimark PLLC

(57) ABSTRACT

A microchip for chemical reaction capable of rapidly performing an experiment irrespective of the types of the chemical substrates used for the experiment under various experimental conditions, wherein a horizontal communication path 13 comprising a plurality of chemical reaction pool portions 11, 12 and grooves communicating these chemical reaction pool portions 11, 12 to each other is formed in the surface of a diamond substrate 10 of minute size forming a substrate, a vertical communication path 20 comprising through-holes vertically communicating the chemical reaction pool portions 11, 12 to each other is provided in the diamond substrate 10, and an opening/closing valve 21 is installed at a communicating portion, and further heating/cooling portions 23, 24 such as a Peltier device are installed at those positions corresponding to the chemical reaction pool portions 11, 12, respectively, whereby a variety of experiments can be performed in a very small space without being restricted by the types of chemical substrates and by varying the experimental conditions.

3 Claims, 5 Drawing Sheets

MICRO-CHIP FOR CHEMICAL REACTION

REFERENCE TO RELATED APPLICATIONS

The present application is the national stage under 35 U.S.C. 371 of international application PCT/JP00/00867, filed Feb. 16, 2000 which designated the United States, and which international application was not published under PCT Article 21(2) in the English language.

TECHNICAL FIELD

The present invention relates to a microchip for a chemical reaction in which various types of chemical reactions can be performed in a microspace.

BACKGROUND OF THE INVENTION

In recent years, there has been advocated a so-called integrated chemical laboratory in which a chemical experiment can be executed in a microspace in a micrometer scale aiming at speedup, labor saving, resource saving, energy saving, space saving and, further, a reduction of experimental waste liquid and wastes, rationalization of repeated experiments and so forth of various types of researches and developments.

Such an integrated chemical laboratory is constituted by forming a process channel of from sub-$\mu$m to 100 $\mu$m on a glass substrate having a size of several centimeters square and has an object of performing a chemical reaction on a micro level, separate and, further, detecting a resultant reaction product in a continuous operation.

However, the above-described integrated chemical laboratory has the following problems yet to be solved:

1. Namely, since a glass substrate is used as a substrate, sufficient corrosion resistance can not be secured depending on chemical substances whereupon there is a fear that an experiment related with such chemical substances can not be executed.
2. Since the glass substrate is low in thermal resistance, there is a fear that an experiment cannot be executed at high temperature.
3. It is considered that an experiment is executed at a high temperature or low temperature by providing, for example, a heating/cooling means on a lower surface of a reaction portion of the glass substrate; however, since the glass substrate is low in thermal conductivity, there is a fear that a sufficient chemical reaction rate cannot be secured.

The present invention can solve the above-described problems and has an object of providing a microchip for a chemical reaction in which an experiment can be executed in a quick manner irrespective of a type of a chemical substance to be subjected to a chemical reaction and under all experimental conditions.

DISCLOSURE OF THE INVENTION

In order to achieve the above-described object, a microchip for a chemical reaction according to the present invention is constituted such that a plurality of chemical reaction pool portions and a horizontal communication path composed of a channel which communicates and connects the plurality of chemical reaction pool portions with each other are formed on the surface of a diamond substrate of a minute size.

The microchip for the chemical reaction according to the present invention is also characterized by having the following constitutions:

1. A vertical communication path composed of a pass-through hole which vertically communicates with one of the chemical reaction pool portions is provided and an opening/closing valve is attached to a communication and connection portion.
2. A heating/cooling means is attached along a periphery or a bottom surface of the chemical reaction pool portions for the purpose of heating/cooling the chemical reaction portions.

BEST MODE FOR CARRYING OUT THE INVENTION

Figure 1:
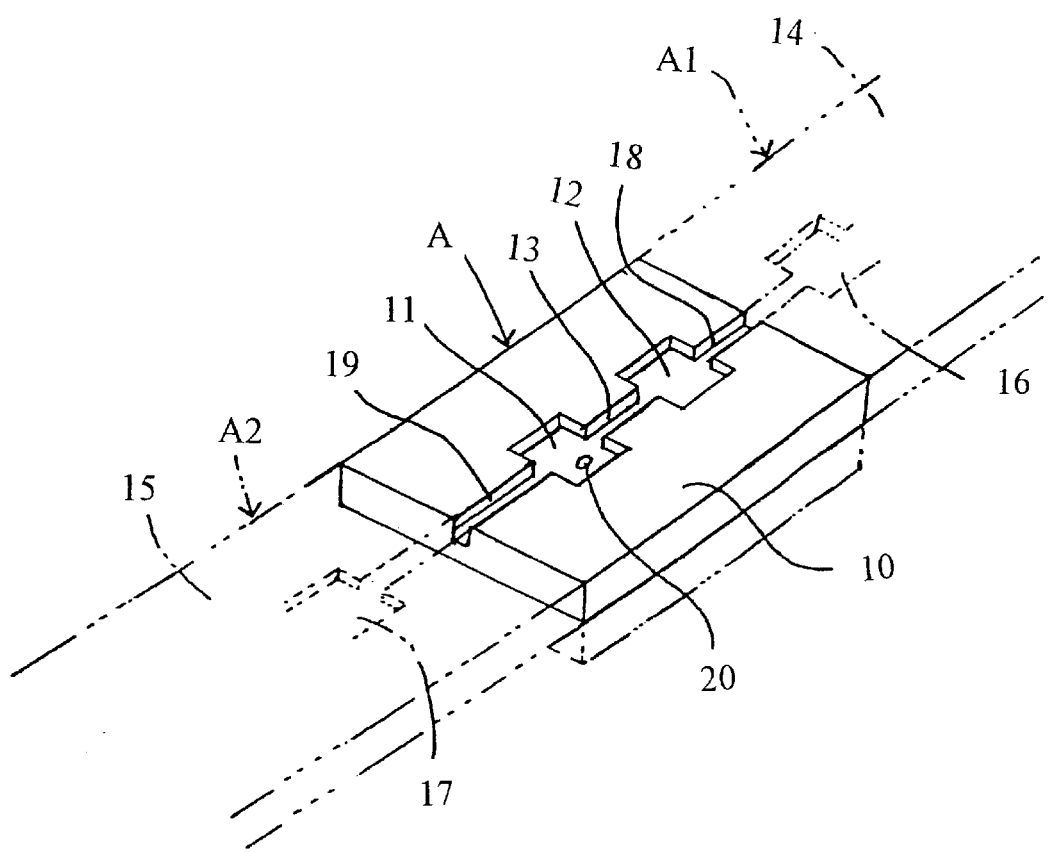
FIG. 1 is a perspective view of a microchip for a chemical reaction according to an embodiment of the present invention.

The present invention is specifically described with reference to preferred embodiments shown in the accompanying drawings.

First of all, an entire constitution of a microchip A for a chemical reaction according to an embodiment of the present invention will now be described with reference to FIGS. 1 to 3.

As shown in the figures, a diamond substrate 10 which comprises the main body of the microchip A for the chemical reaction is made of a rectangular plate having a width and length of several cm each and a thickness of sub-$\mu$m to several hundred $\mu$m. And, on the surface of a side of the diamond substrate 10, are formed a plurality of chemical reaction pool portions 11, 12 and a horizontal communication path 13 composed of a channel which communicates and connects these chemical reaction pool portions 11, 12 therebetween. Further, on the surface of the side of the diamond substrate 10, are provided horizontal communication paths 18, 19 composed of channels for communicating and connecting chemical reaction pool portions 16, 17 which have similarly been provided in respective diamond substrates 14, 15 of other microchips A1, A2 for chemical reactions that are placed adjacent to the microchip A for the chemical reaction on a horizontal plane with the chemical reaction pool portions 11, 12 of the microchip A for the chemical reaction, respectively.

Figure 2:
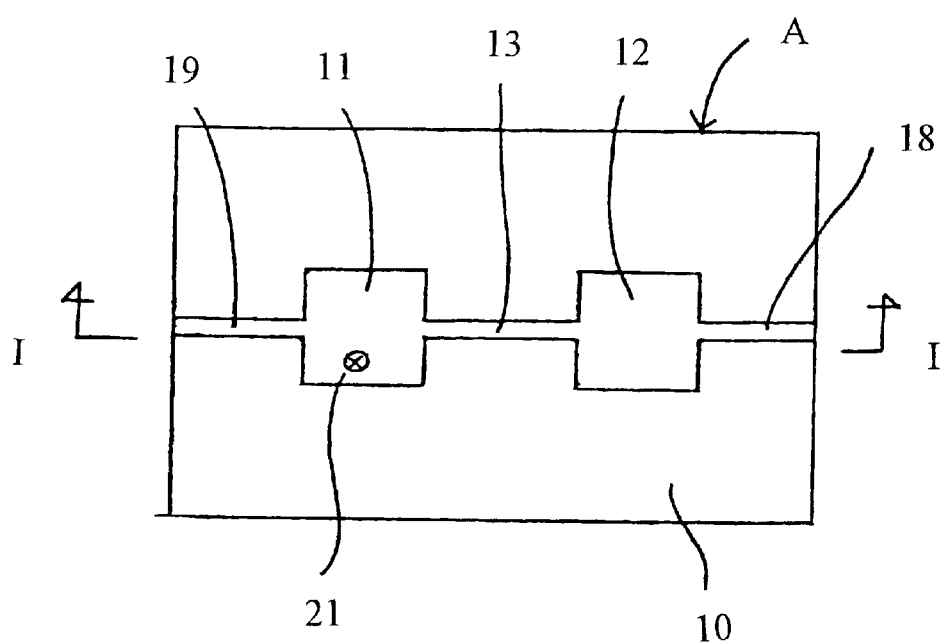
FIG. 2 is a plan view of a microchip for a chemical reaction according to an embodiment of the present invention.
Figure 3:
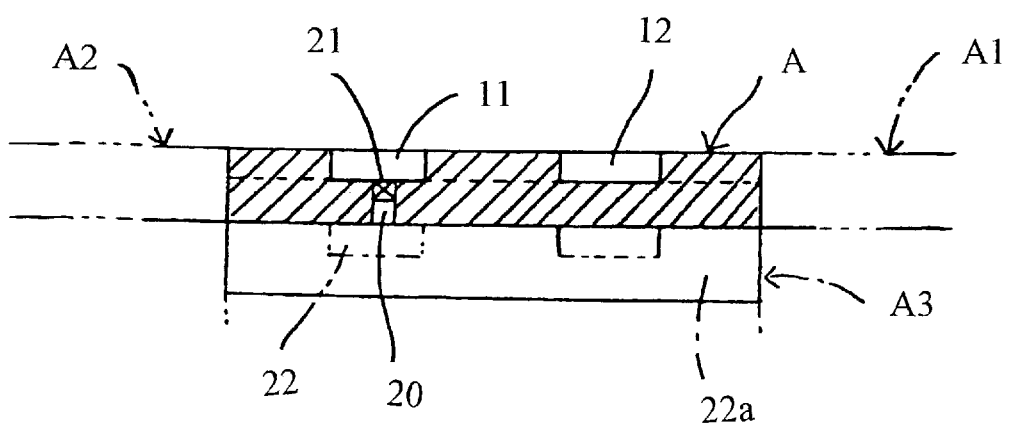
FIG. 3 is a sectional view taken on line I—I of FIG. 2.

Furthermore, as shown in FIGS. 1 to 3, in the present embodiment, on the diamond substrate 10, is formed a vertical communication path 20 composed of a pass-through hole for vertically communicating and connecting with the chemical reaction pool portion 11; attached is an opening/closing valve 21 to a communication and connection portion between the chemical reaction pool portion 11 and the vertical communication path 20. Therefore, as shown in FIG. 3, the chemical reaction pool portion 11 can be communicated and connected with a chemical reaction pool portion 22 provided on a diamond substrate 22a of a microchip A3 for a chemical reaction which is provided under the microchip A for the chemical reaction and, further, communication therebetween can be cut off by closing the opening/closing valve 21. Further, the opening/closing valve 21 can be formed from, for example, a valve plate having a property of shape-memory alloy.

Figure 4:
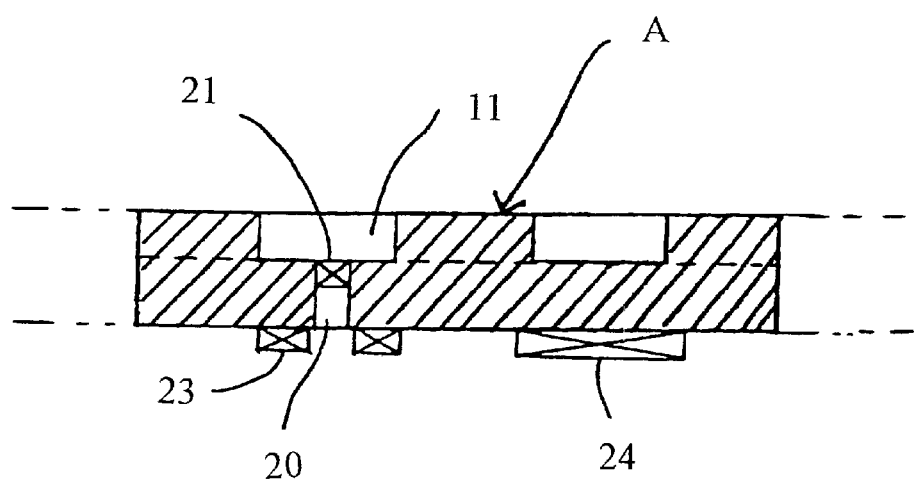
FIG. 4 is a sectional view of a microchip for a chemical reaction according to an embodiment of the present invention in a state in which a heating/cooling means is attached.

Furthermore; as shown in FIG. 4, it is considered that a heating/cooling means 23, 24 such as a Peltier device can be attached to portions which correspond to the chemical reaction pool portions 11, 12 under the diamond substrate 10 of the microchip A for the chemical reaction. By this arrangement, reactions of chemical substances in the chemical reaction pool portions 11, 12 can be promoted.

Next, a chemical reaction using the microchip A for the chemical reaction having the above-described configuration will be described.

First of all, a plurality of chemical substances in liquid, gas and solid forms which are subjected to experiments are each flowed or introduced into the chemical reaction pool portion 11 to effect a chemical reaction and after the reaction the resulting product is sent to the chemical reaction pool portion 12 or the chemical reaction pool portion 22 through the horizontal communication path 13 or the vertical communication path 20 where a subsequent chemical reaction, a component analysis or the like is performed.

On this occasion, since substrates of the microchips A, A3 (same is also applicable to A1, A2) for the chemical reactions are composed of diamond substrates 10, 22a (14, 15), they have high corrosion resistance to all chemical substances and can perform a variety of chemical experiments in respective microspaces thereof free of restrictions irrespective of types of chemical substances.

Further, since the diamond substrates 10, 14, 15, 22a are excellent in thermal conductivity, for example, the heating/cooling means 23, 24 such as a Peltier device and the like are attached to portions corresponding to the chemical reaction pool portions 11, 12 to enhance a chemical reaction rate thereby efficiently executing an experiment.

Figure 5:
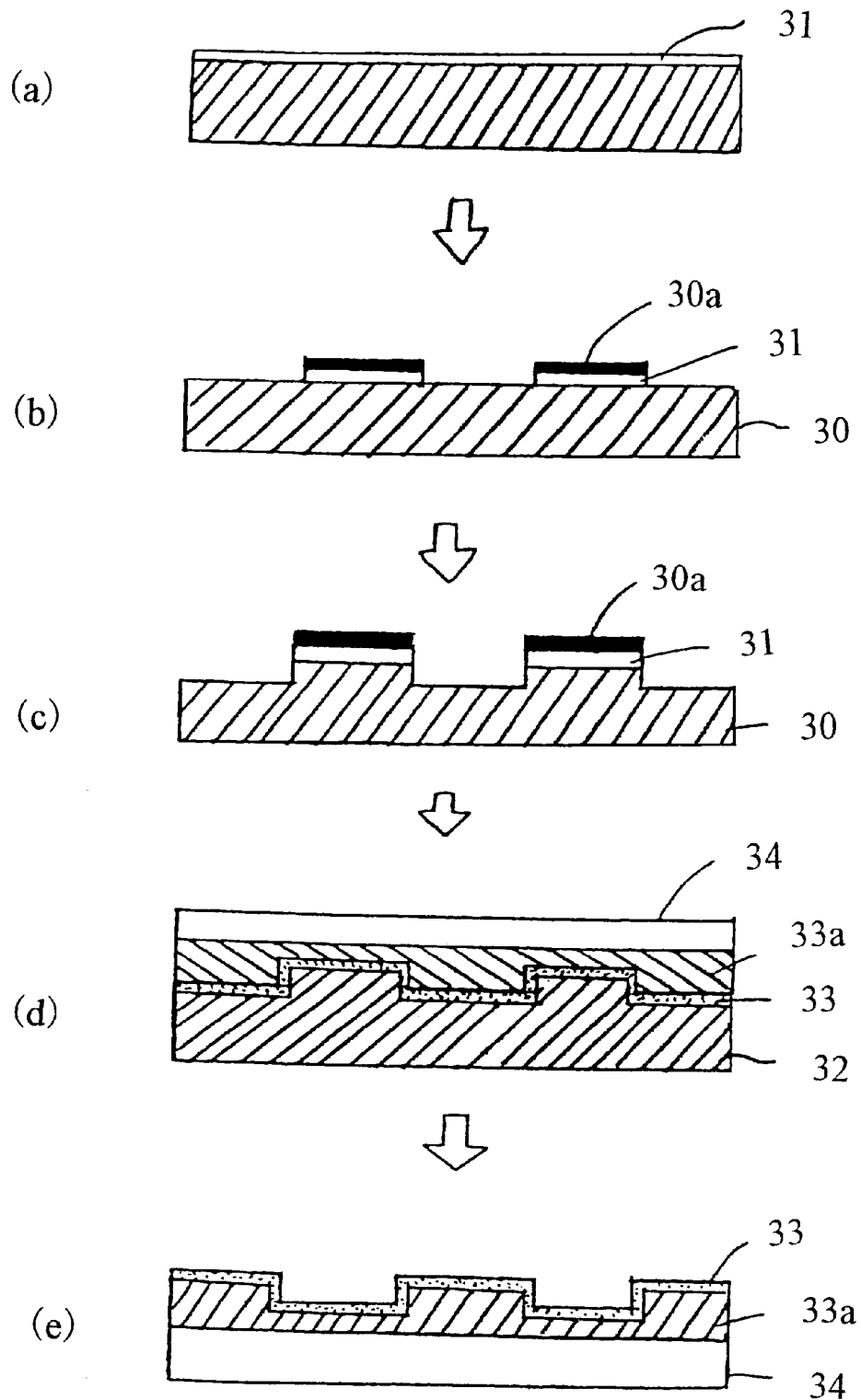
FIG. 5 is an explanatory view of production processes of a diamond substrate of a microchip for a chemical reaction according to an embodiment of the present invention.

In the diamond substrates 10, 14, 15, 22a of the microchips A to A3 for chemical reactions, the chemical reaction pool portions 11, 12, 16, 17, 22 can be formed and machined by melting and removing by means of a diamond laser or the like; however, as is described below with reference to FIGS. 5, the chemical reaction pool portions 11, 12, 16, 17, 22 having a clear cross-section can be formed on silicon 30 by a transfer method.

Namely, as shown in FIG. 5(a), a silicon oxide film 31 is grown on the surface of the silicon 30. As shown in FIG. 5(b), patterning is performed using a photoresist 30a. Thereafter, the silicon oxide film 31 is removed by performing isotropic etching using hydrofluoric acid (HF).

As shown in FIG. 5(c), the silicon 30 is subjected to anisotropic etching using a tetramethylammoniumhydroxide solution $((CH_3)_4NOH)$.

As shown in FIG. 5(d), using a resultant trapezoid-shaped silicon substrate 32 as a mold, diamond 33 is grown by a hot-filament CVD method. After the diamond 33 is grown, the surface of a thus-grown diamond 33 is coated with electroconductive epoxy 33a which is then placed on a platinum plate and fixed thereto by being hardened by heat.

As shown in FIG. 5(e), the silicon substrate 32 is removed in a mixture of hydrofluoric acid and nitric acid $(HF+HNO_3)$ to form chemical reaction pool portions 11, 12, 16, 17 and 22.

As a method of forming the silicon substrate 32 in a trapezoid state as a mold, there is also a method in which, instead of growing the silicon oxide film 31 on the surface of the silicon 30 described with reference to FIG. 5(a), patterning is performed on the silicon substrate using the photoresist. Further, there is a method of etching a silicon surface using sulfur hexafluoride as an etching gas by means of an RIE (reactive ion etching) method, instead of performing the etching using hydrofluoric acid (HF) as described with reference to FIG. 5(b). Thereafter, these methods are followed by a process of growing diamond 33 by the hot-filament CVD method as shown in the above-described FIG. 5 (d).

POSSIBILITY OF USE IN THE INVENTION

As has been described above, in the present invention, since a diamond substrate is used as a substrate of a microchip for a chemical reaction, the substrate of the microchip has a high resistance to all types of chemical substances and a variety of experiments can be conducted in a microspace thereof without being restricted by types of chemical substances in a manner different from a glass substrate.

Further, in the diamond substrate, provided is a vertical communication path for vertically communicating and connecting with a chemical reaction pool portion and an opening/closing valve in a communication and connection portion thereby forming a three-dimensional chemical experiment facility in a compact space of which a variety of experiments can be conducted.

Further, since the diamond substrate is excellent in thermal conductivity, a provision of a heatig/cooling means such as Peltier device and the on a portion corresponding to the chemical reaction pool portion enhances a reaction rate, thereby efficiently conducting the experiment.

What is claimed is:

1. A microchip for a chemical reaction comprising a plurality of chemical reaction pool portions and a horizontal communication path composed of a channel which communicates and connects said plurality of chemical reaction pool portions with each other and a heating/cooling Peltier element which is attached along a periphery or a bottom surface of the chemical reaction pool portions are formed on the surface of a diamond substrate of a minute size.

2. The microchip for a chemical reaction as set forth in claim 1, wherein a vertical communication path composed of a pass-through hole which vertically communicates with one of said chemical reaction pool portions is provided on said diamond substrate and an opening/closing valve is attached to a communication and connection portion.

3. The microchip for chemical reaction according to claim 1 wherein the opening/closing valve is formed from a valve plate made of a shape-memory alloy.

* * * * *